(12) United States Patent
Lu et al.

(10) Patent No.: US 11,000,701 B2
(45) Date of Patent: May 11, 2021

(54) DUAL-LAYER DETECTOR FOR SOFT TISSUE MOTION TRACKING

(71) Applicant: VAREX IMAGING CORPORATION, Salt Lake City, UT (US)

(72) Inventors: Minghui Lu, Fremont, CA (US); Richard Aufrichtig, Palo Alto, CA (US); Joachim Steiger, Livermore, CA (US)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 86 days.

(21) Appl. No.: 16/024,747

(22) Filed: Jun. 30, 2018

(65) Prior Publication Data
US 2019/0038918 A1 Feb. 7, 2019

Related U.S. Application Data

(60) Provisional application No. 62/539,944, filed on Aug. 1, 2017.

(51) Int. Cl.
*A61B 6/00* (2006.01)
*A61N 5/10* (2006.01)
(Continued)

(52) U.S. Cl.
CPC .............. *A61N 5/1049* (2013.01); *A61B 6/42* (2013.01); *A61B 6/4208* (2013.01);
(Continued)

(58) Field of Classification Search
CPC ...... A61N 5/10; A61N 5/1048; A61N 5/1049; A61N 2005/1054; A61N 2005/1061;
(Continued)

(56) References Cited

U.S. PATENT DOCUMENTS

| 4,626,688 A | * | 12/1986 | Barnes | ................... | A61B 6/032 |
| | | | | | 250/361 R |
| 4,963,746 A | * | 10/1990 | Morgan | ................... | A61B 6/06 |
| | | | | | 250/363.02 |

(Continued)

OTHER PUBLICATIONS

International Search Report and Written Opinion of the International Searching Authority, International application No. PCT/US2018/041535, dated Oct. 24, 2018.
(Continued)

*Primary Examiner* — Allen C. Ho
(74) *Attorney, Agent, or Firm* — Su IP Consulting

(57) ABSTRACT

An imaging apparatus includes a first X-ray detector that includes: a low energy scintillator operable to convert an incident X-ray spectrum into a first set of light photons; a first light imaging sensor operable to generate a set of low energy image signals from the first set of light photons, wherein a first exit radiation is a remainder portion of the first incident radiation after the X-ray spectrum passes through the low energy scintillator and the first light imaging sensor; an energy-separation filter operable to absorb or reflect at least a portion of the energy of the first exit X-ray spectrum and convert the first exit X-ray spectrum into a second exit X-ray spectrum; a second X-ray detector that includes: a high energy scintillator operable to convert the second exit X-ray spectrum into a second set of light photons; a second light imaging sensor operable to generate a set of high energy image signals from the second set of light photons; and a processor configured to: generate a high-energy image that is based on the set of high energy image signals and a low-energy image that is based on the set of low energy image signals; and perform a comparison of the high-energy image from the low-energy image to generate a soft tissue image.

19 Claims, 6 Drawing Sheets

(51) Int. Cl.
| | |
|---|---|
| *G01T 1/20* | (2006.01) |
| *G06T 11/00* | (2006.01) |
| *G06T 7/20* | (2017.01) |
| *G06T 7/246* | (2017.01) |
| *G01T 1/00* | (2006.01) |
| *G06T 5/50* | (2006.01) |
| *G01T 1/24* | (2006.01) |
| *A61B 6/03* | (2006.01) |

(52) U.S. Cl.
CPC .......... *A61B 6/4216* (2013.01); *A61B 6/4225* (2013.01); *A61B 6/4233* (2013.01); *A61B 6/4241* (2013.01); *A61B 6/4291* (2013.01); *A61B 6/44* (2013.01); *A61B 6/4452* (2013.01); *A61B 6/482* (2013.01); *A61B 6/50* (2013.01); *A61B 6/52* (2013.01); *A61B 6/5205* (2013.01); *A61B 6/5258* (2013.01); *A61N 5/10* (2013.01); *A61N 5/1039* (2013.01); *A61N 5/1048* (2013.01); *A61N 5/1075* (2013.01); *A61N 5/1077* (2013.01); *G01T 1/00* (2013.01); *G01T 1/20* (2013.01); *G01T 1/2006* (2013.01); *G01T 1/2008* (2013.01); *G01T 1/2018* (2013.01); *G01T 1/242* (2013.01); *G06T 5/50* (2013.01); *G06T 7/20* (2013.01); *G06T 7/248* (2017.01); *G06T 11/005* (2013.01); *A61B 6/032* (2013.01); *A61B 6/505* (2013.01); *A61B 6/5264* (2013.01); *A61N 2005/1054* (2013.01); *A61N 2005/1061* (2013.01); *A61N 2005/1062* (2013.01); *A61N 2005/1076* (2013.01); *A61N 2005/1091* (2013.01); *G06T 2207/10116* (2013.01); *G06T 2207/20224* (2013.01); *G06T 2207/30008* (2013.01); *G06T 2211/408* (2013.01)

(58) Field of Classification Search
CPC .... A61N 2005/1062; A61N 2005/1091; G01T 1/20; G01T 1/2006; G01T 1/24; G01T 1/242; G01T 1/2018; A61B 6/42; A61B 6/4208; A61B 6/4216; A61B 6/4241; A61B 6/482; A61B 6/032; A61B 6/4233; A61B 6/44; A61B 6/4452; A61B 6/50; A61B 6/505; A61B 6/52; A61B 6/5205; A61B 6/5258; A61B 6/5264
USPC ................. 378/5, 19, 65, 98.8, 98.9, 98.11; 250/370.09
See application file for complete search history.

(56) References Cited

U.S. PATENT DOCUMENTS

| | | | | |
|---|---|---|---|---|
| 5,049,746 | A * | 9/1991 | Ito | A61B 6/482 250/583 |
| 5,138,167 | A * | 8/1992 | Barnes | G01T 1/2018 250/363.02 |
| 5,402,338 | A * | 3/1995 | Ito | G06T 5/004 250/583 |
| 6,125,166 | A * | 9/2000 | Takeo | A61B 6/4241 378/62 |
| 6,285,740 | B1 * | 9/2001 | Seely | H05G 1/20 250/367 |
| 6,501,819 | B2 * | 12/2002 | Unger | A61B 6/405 378/207 |
| 6,842,502 | B2 * | 1/2005 | Jaffray | A61B 6/032 378/65 |
| 7,006,679 | B2 * | 2/2006 | Funahashi | G06T 5/50 378/98.11 |
| 7,010,092 | B2 * | 3/2006 | Winsor | A61B 6/482 250/367 |
| 7,248,726 | B2 * | 7/2007 | Sasada | G06T 5/50 378/98.12 |
| 7,263,165 | B2 * | 8/2007 | Ghelmansarai | A61N 5/1049 250/370.09 |
| 7,453,976 | B1 * | 11/2008 | Yin | A61B 6/032 378/65 |
| 7,634,061 | B1 * | 12/2009 | Tümer | G01T 1/247 378/62 |
| 7,696,481 | B2 * | 4/2010 | Tkaczyk | G01T 1/2985 250/363.02 |
| 7,769,138 | B2 * | 8/2010 | Dafni | A61B 6/4233 378/98.11 |
| 7,860,215 | B2 * | 12/2010 | Long | A61B 6/032 378/65 |
| 7,873,141 | B2 * | 1/2011 | Imai | A61B 6/032 378/5 |
| 7,876,881 | B2 * | 1/2011 | Jeffery | A61B 6/032 378/10 |
| 7,945,021 | B2 * | 5/2011 | Shapiro | A61B 6/032 378/65 |
| 7,968,853 | B2 * | 6/2011 | Altman | A61B 6/032 250/366 |
| 8,019,044 | B2 * | 9/2011 | Shkumat | A61B 6/4035 378/156 |
| 8,265,728 | B2 * | 9/2012 | MacMahon | A61B 6/463 378/5 |
| 8,391,439 | B2 * | 3/2013 | Levene | G01T 1/2018 250/370.09 |
| 8,416,917 | B2 * | 4/2013 | Maltz | A61N 5/10 378/65 |
| 8,440,978 | B2 * | 5/2013 | Morf | G01T 1/2018 250/370.09 |
| 8,442,184 | B2 * | 5/2013 | Forthmann | A61B 6/032 378/5 |
| 8,483,352 | B2 * | 7/2013 | Hoffman | A61B 6/032 378/19 |
| 8,483,353 | B2 * | 7/2013 | Hoffman | A61B 6/032 378/19 |
| 8,488,736 | B2 * | 7/2013 | Hoffman | A61B 6/032 378/19 |
| 8,525,121 | B2 * | 9/2013 | Nakatsugawa | G01T 1/242 250/367 |
| 8,536,547 | B2 * | 9/2013 | Maurer, Jr. | A61N 5/1081 250/492.3 |
| 8,559,596 | B2 * | 10/2013 | Thomson | G06T 7/0014 378/65 |
| 8,571,178 | B2 * | 10/2013 | Sendai | A61B 6/4042 378/157 |
| 8,653,471 | B2 * | 2/2014 | Proksa | A61B 6/032 250/363.01 |
| 8,873,713 | B2 * | 10/2014 | Suyama | G01V 5/005 250/370.09 |
| 8,917,813 | B2 * | 12/2014 | Maurer, Jr. | A61B 6/4014 378/65 |
| 8,981,310 | B2 * | 3/2015 | Suyama | G01V 5/005 250/370.11 |
| 8,989,846 | B2 * | 3/2015 | Kuduvalli | A61B 6/00 378/181 |
| 9,012,857 | B2 * | 4/2015 | Levene | G01T 1/2018 250/370.09 |
| 9,040,924 | B2 * | 5/2015 | Lewellen | A61B 6/037 250/361 R |
| 9,182,504 | B2 * | 11/2015 | Nishino | G01T 1/2018 |
| 9,216,302 | B2 * | 12/2015 | Kuwahara | A61N 5/1039 |
| 9,265,971 | B2 * | 2/2016 | Baltes | A61N 5/1071 |
| 9,268,037 | B2 * | 2/2016 | Partain | G01T 1/2018 |
| 9,271,681 | B2 * | 3/2016 | Uebayashi | A61B 6/032 |
| 9,315,726 | B2 * | 4/2016 | Ronda | C09K 11/7774 |
| 9,345,443 | B2 * | 5/2016 | Bertens | A61B 6/032 |
| 9,354,328 | B2 * | 5/2016 | Vogtmeier | G01T 1/2008 |
| 9,415,240 | B2 * | 8/2016 | Jordan | A61N 5/1083 |
| 9,423,514 | B2 * | 8/2016 | Roessl | G01T 1/20 |
| 9,433,391 | B2 * | 9/2016 | Miyazaki | A61B 6/4241 |
| 9,533,173 | B2 * | 1/2017 | Manzke | A61N 5/1064 |
| 9,576,391 | B2 * | 2/2017 | Ra | G06T 11/005 |
| 9,588,235 | B2 | 3/2017 | Weisfield et al. | |

(56) References Cited

U.S. PATENT DOCUMENTS

| | | | |
|---|---|---|---|
| 9,610,057 B2* | 4/2017 | Zou | A61B 6/4405 |
| 9,616,251 B2* | 4/2017 | Filiberti | A61N 5/1075 |
| 9,687,200 B2* | 6/2017 | Maurer, Jr. | A61N 5/1049 |
| 9,700,268 B2* | 7/2017 | Kang | A61B 6/542 |
| 9,746,581 B2* | 8/2017 | Whittum | G01V 5/0041 |
| 9,784,850 B2* | 10/2017 | Da Silva Rodrigues | G01T 1/1603 |
| 9,901,318 B2* | 2/2018 | Kang | G01N 23/04 |
| 9,919,166 B2* | 3/2018 | Kontaxis | A61N 5/1038 |
| 9,949,710 B2* | 4/2018 | Kang | A61B 6/481 |
| 9,980,686 B2* | 5/2018 | Proksa | A61B 6/4241 |
| 10,012,741 B2* | 7/2018 | Saruta | G01T 1/2002 |
| 10,234,572 B2* | 3/2019 | Hadjioannou | G01T 1/2985 |
| 10,271,804 B2* | 4/2019 | Ohga | A61B 6/469 |
| 10,295,678 B2* | 5/2019 | Tanabe | G01T 1/20 |
| 10,342,996 B2* | 7/2019 | Jordan | A61N 5/1037 |
| 10,345,459 B2* | 7/2019 | Kuwabara | A61B 6/54 |
| 10,444,166 B2* | 10/2019 | Onishi | G01N 23/083 |
| 10,463,331 B2* | 11/2019 | Goshen | A61B 6/482 |
| 10,485,503 B2* | 11/2019 | Schaefer | G01T 1/2985 |
| 10,682,116 B2* | 6/2020 | Mollov | H04N 5/32 |
| 2007/0242802 A1 | 10/2007 | Dafni | |
| 2010/0284628 A1 | 11/2010 | Uebayashi et al. | |
| 2012/0235047 A1 | 9/2012 | Lewellen et al. | |
| 2014/0185765 A1 | 7/2014 | Kang et al. | |
| 2014/0321613 A1 | 10/2014 | Whittum et al. | |
| 2016/0209515 A1 | 7/2016 | Da Silva Rodrigues et al. | |
| 2017/0112456 A1 | 4/2017 | Ohga et al. | |
| 2019/0159749 A1 | 5/2019 | Mollov et al. | |

OTHER PUBLICATIONS

Wesley A. Bowman et al., Optimizing dual-energy x-ray parameters for the ExacTrac clinical stereoscopic imaging system to enhance soft-tissue imaging, Medical Physics, Mar. 2017, pp. 823-831, vol. 44, No. 3.

Cynthia H. McCollough, PhD et al., "Dual- and Multi-Energy CT: Principles, Technical Approaches, and Clinical Applications", Radiology RSNA, Sep. 2015, pp. 637-653, vol. 276, No. 3.

Martin J. Menten et al., "Using dual-energy x-ray imaging to enhance automated lung tumor tracking during real-time adaptive radiotherapy", Medical Physics, Dec. 2015, pp. 6987-6998, vol. 42, No. 12.

Rakesh Patel et al., "Markerless motion tracking of lung tumors using dual-energy fluoroscopy", Medical Physics, Jan. 2015, pp. 254-262, vol. 42, No. 1.

Tracy Sherertz, MD et al., "Prospective Evaluation of Dual-Energy Imaging in Patients Undergoing Image Guided Radiation Therapy for Lung Cancer: Initial Clinical Results", International Journal of Radiation Oncology-Biology-Physics, 2013, pp. 525-531, vol. 89, No. 3.

Hideki Fujita et al., "Effectiveness of the single-shot dual-energy subtraction technique for portal images", Journal of Applied Clinical Medical Physics, Fall 2011, pp. 24-33, vol. 12, No. 4.

Tong Xu et al., "Dynamic dual-energy chest radiography: a potential tool for lung tissue motion monitoring and kinetic study", Physics Medical Biology, Feb. 21, 2011, pp. 1191-1205, vol. 56, No. 4.

J. H. Siewerdsen et al., "High-Performance Dual-Energy Imaging with a Flat-Panel Detector: Imaging Physics from Blackboard to Benchtop to Bedside", SPIE Medical Imaging, 2006, pp. 10, vol. 6142.

Frank Fischbach et al., "Dual-Energy Chest Radiography with a Flat-Panel Digital Detector: Revealing Calcified Chest Abnormalities", AJR:181, Dec. 20013, pp. 1519-1524.

Shenchang Eric Chen et al., "View Interpolation for Image Synthesis", Apple Computer, Inc., 1993, pp. 279-288.

International Preliminary Report on Patentability, International Application No. PCT/US2018/041535, dated Feb. 13, 2020.

* cited by examiner

DUAL-LAYER DETECTOR FOR SOFT TISSUE MOTION TRACKING

CROSS-REFERENCE TO RELATED APPLICATIONS

The present application claims the benefit of U.S. Provisional Application No. 62/539,944, filed Aug. 1, 2017. The U.S. Provisional Application, including any appendices or attachments thereof, is hereby incorporated by reference in its entirety.

BACKGROUND

Unless otherwise indicated herein, the approaches described in this section are not prior art to the claims in this application and are not admitted to be prior art by inclusion in this section.

Use of radiotherapy (RT) to treat tumors, and other areas of targeted tissue, is widely known. One challenge associated with using radiation to treat tumors is to precisely locate a tumor in a patient's body during radiation therapy. When the treatment is applied accurately to the targeted tumor in the patient, the impact of the treatment on the surrounding healthy tissue is minimized.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
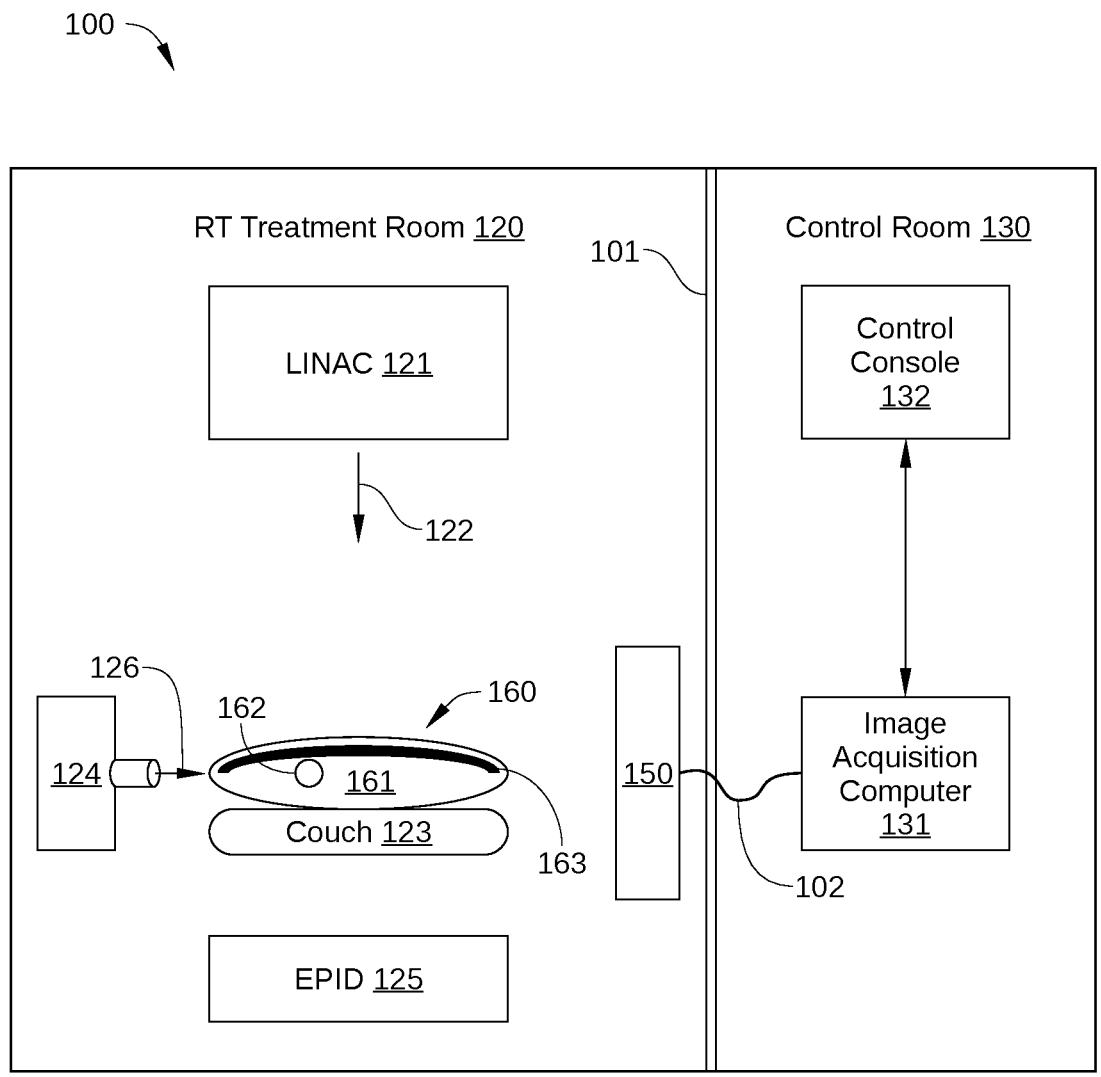
FIG. 1 illustrates a clinical environment in which an embodiment of the present disclosure can be integrated.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

As used herein, radiation refers to ionizing radiation, such as X-rays and gamma rays. X-rays can be used in diagnostic imaging and treatment (e.g., RT). For simplicity and consistency of terminology used, the radiation (e.g., radiation detectors) described herein may be referred to X-rays (e.g., X-ray detectors) but also include other ionizing radiation.

As noted above, when RT treatment is applied accurately to targeted tissue in a patient, there is minimal impact on healthy tissue surrounding the targeted tissue. However, the motion of soft tissue organs (e.g., the lung, prostate, or liver) during RT, for example due to patient respiration, can alter the location of targeted tissue, and may cause inaccurate radiation delivery during RT treatment. To reduce the effects of the motion of soft tissue organs, there are some tracking approaches currently known in the art that employ fluoroscopy to obtain real-time moving images of the target tissue. However, bony structures adjacent to the target tissue make fluoroscopy-based motion tracking challenging, since the soft tissue of interest can be occluded by such bony structures. Alternatively, techniques for visually separating bones from the soft tissues have been proposed in which a patient is exposed to higher energy X-rays and lower energy X-rays, respectively. However, these techniques generally involve multiple X-ray exposures and, as a result, a patient is exposed to higher imaging doses. And with these techniques the time offset between the high energy X-ray images and the low energy X-ray images can cause motion blurred images and reduced accuracy in motion tracking of the targeted tissue.

In some embodiments, the disclosure provides devices and methods to enhance the visualization of soft tissue motion in an image sequence without increasing the imaging dose for the patient. More specifically, the example devices and methods disclosed herein can remove and/or reduce the visual contribution of dense materials (e.g., bones) to such an image sequence, thereby facilitating the accurate radiation treatment of targeted tissues. In some embodiments, an imaging apparatus includes a first X-ray detector 220 stacked onto a second X-ray detector 230 with an energy separation filter 240 disposed there between, where the first and second X-ray detector each include a scintillator and light imaging sensor. In some embodiments, the first X-ray detector 220 and the second X-ray detector 230 can each acquire an X-ray image of a target region from a single radiation exposure, where the image acquired by the first X-ray detector 220 is at a first mean energy and the image acquired by the second X-ray detector is at a second mean energy that is different (typically higher) than the first mean energy.

In some embodiments, the first X-ray detector acquires an X-ray image of the target region. Simultaneously, the second X-ray detector acquires an X-ray image of the target region using X-rays at a higher mean energy passing through the first detector and the filter. A soft-tissue-only image of the target region is then generated, in which visibility of soft tissue is enhanced by the removal of obscuring dense tissues. Such a soft-tissue-only image enables more accurate detection of motion of soft tissue organs or structures in the target region, even when obscured by bony structures. Thus, embodiments of the disclosure facilitate motion detection of soft tissue via dual-energy imaging, in which two images are acquired with a single radiation exposure.

FIG. 1 illustrates a clinical environment 100 in which an embodiment of the present disclosure can be integrated. Clinical environment 100 includes a radiotherapy (RT) treatment room 120 and a control room 130, separated by a shielded wall 101. RT treatment room 120 includes a linear accelerator (LINAC) 121 that generates a megavolt (MV) treatment beam 122 of high energy X-rays (or in some embodiments electrons), a patient couch 123, a kilovolt (kV) X-ray source 124, a dual-layer X-ray detector 150, and, in some embodiments, a MV electronic portal imaging device (EPID) 125. Control room 130 includes an image acquisition computer 131 communicatively coupled to dual-layer X-ray detector 150 via an acquisition cable 102, and an associated control console 132.

Also shown in FIG. 1 is a patient 160, positioned on patient couch 123 for RT treatment. Patient 160 includes soft tissues 161, such as organs and a target region 162. Target region 162 may be, for example, a tumor to receive RT treatment. Patient 160 also includes bony structures 163, such as ribs, pelvic bones, and the like. Bony structures 163 can obscure soft tissues 161 and target region 162 in X-ray images, thereby reducing the accuracy of motion detection of target region 162 during RT treatment.

LINAC 121 customizes MV treatment beam 122 to conform to the shape of a tumor in target region 162 of patient 160. Thus, LINAC 121 destroys or damages cancer cells while sparing surrounding normal tissue when the location of target region 162 is precisely known. KV X-ray source 124 is an X-ray source for generating an imaging beam 126 directed toward dual-layer X-ray detector 150 for imaging target region 162 and surrounding areas during RT treatment. For example, in some embodiments, clinical environment 100 is employed for image-guided radiation therapy (IGRT), which uses image guidance procedures for target localization before and during treatment. In such embodiments, the X-ray images used to precisely monitor the current location of target region 162 are generated with kV X-ray source 124 and dual-layer X-ray detector 150. One embodiment of dual-layer X-ray detector 150 is described below in conjunction with FIG. 2.

Figure 2:
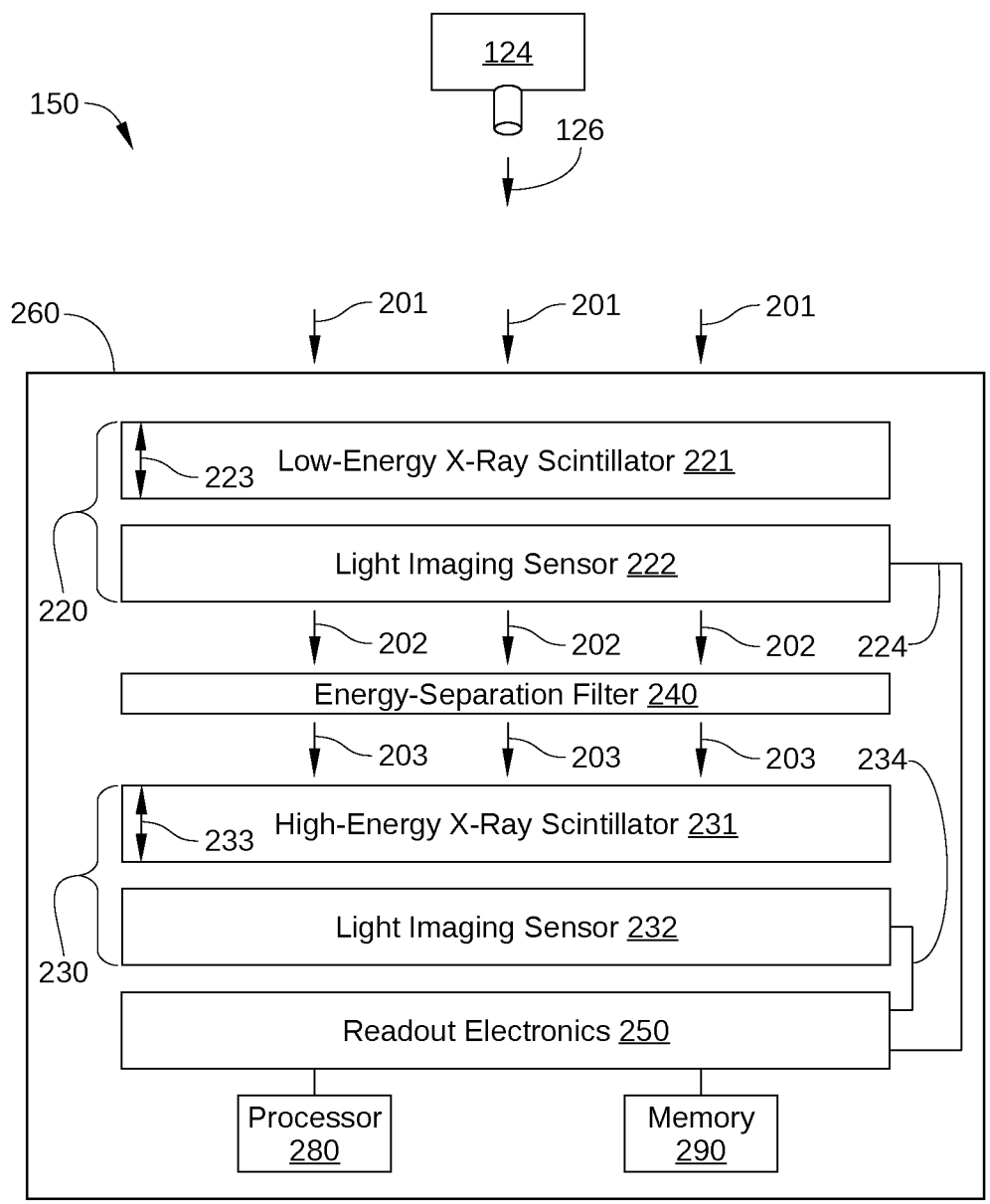
FIG. 2 schematically illustrates a cross-sectional view of a dual-layer X-ray detector, according to various embodiments of the present disclosure.

FIG. 2 schematically illustrates a cross-sectional view of dual-layer X-ray detector 150, according to various embodiments of the present disclosure. Dual-layer X-ray detector 150 includes a low-energy X-ray sensor 220, a high-energy X-ray sensor 230, and an energy-separation filter 240. Dual-layer X-ray detector 150 may also include readout electronics 250, a processor 280, and a memory 290, all disposed within a detector enclosure 260. Dual-layer X-ray detector 150 can be employed in many X-ray based imaging applications, such as cone beam computed tomography (CBCT), radiography, fluoroscopy, portal imaging, and nondestructive testing (NDT). More specifically, dual-layer X-ray detector 150 enables dual energy imaging to generate a soft-tissue-only image of target region 162 by performing a weighted subtraction of a high-energy image of target region 162 from a low-energy image of target region 162. Alternatively, in some embodiments dual-layer X-ray detector 150 enables dual energy imaging to generate a bone image of target region 162 by performing a weighted subtraction of a low-energy image of target region 162 from a high-energy image of target region 162.

Processor 280 controls dual-layer X-ray detector 150 and/or coordinates communication between dual-layer X-ray detector 150 and image acquisition computer 131, and is communicatively coupled to memory 290 and/or a non-volatile data storage medium such as a solid-state drive. Processor 280 may be any suitable processor implemented as a central processing unit (CPU), an application-specific integrated circuit (ASIC), a field programmable gate array (FPGA), any other type of processing unit, or a combination of different processing units. In general, processor 280 may be any technically feasible hardware unit capable of processing data and/or executing software applications residing in memory 290, including an operating system (OS), and, in some embodiments, X-ray image acquisition and/or generation. Processor 280 is configured to read data from and write data to memory 290. Memory 290 may include a random access memory (RAM) module, a flash memory unit, any other type of memory unit, or a combination thereof. Memory 290 may include various software programs that can be executed by processor 280 and application data associated with said software programs and/or may be used for data storage. In the embodiment illustrated in FIG. 2, memory 290 is depicted as a separate device from processor 280, but in other embodiments memory 290 can be included in processor 280.

Low-energy X-ray sensor 220 includes a low-energy X-ray scintillator 221 and a light imaging sensor 222 that is closely coupled thereto. Low-energy X-ray sensor 220 further includes sensor-to-electronics interconnects 224 that connect each of a plurality pixel sensors in light imaging sensor 222 to readout electronics 250. Low-energy X-ray scintillator 221 includes a scintillator material that is excited by incident X-rays and emits light, which is detected by light imaging sensor 222. Low-energy X-ray scintillator 221 may be formed from one or more material layers including, but not limited to, gadolinium oxisulfide ($Gd_2O_2S$:Tb or GdOx), cadmium tungstate ($CdWO_4$), bismuth germanate ($Bi_4Ge_3O_{12}$ or BGO), cesium iodide (CsI), or cesium iodide thallium (CsI:Tl)), among others.

Low-energy X-ray sensor 220 is configured to convert a portion of incident X-rays 201 to light via low-energy X-ray scintillator 221. Low-energy X-ray sensor 220 is also configured to measure the light converted from incident X-rays 201 at each of a plurality of pixel locations within light imaging sensor 222. In some embodiments, a thickness 223 of the scintillator material of low-energy X-ray scintillator 221 is selected so that low-energy X-ray scintillator 221 generates sufficient light for sensors in light imaging sensor 222 to generate a usable X-ray image, but still transmits a significant fraction of incident X-rays 201, for example 1% to 50%. For example, in one embodiment, low-energy X-ray scintillator 221 includes CsI as a scintillator material having a thickness 223 of between about 100 microns (μm) to about 550 μm.

Light imaging sensor 222 includes a plurality of light sensors, such as amorphous silicon photodiodes, complementary metal-oxide-semiconductor-based (CMOS-based) photodiodes, and/or charge-coupled device-based (CCD-based) imaging devices. Each photodiode or other light sensor (not shown) of light imaging sensor 222 is a pixel sensor that generates a signal (e.g., a voltage that is proportional to incident light intensity) for a different pixel of what will eventually become a digital image. For example, in one embodiment, light imaging sensor 222 includes an array of 2880×2880 pixels and has a pixel size of 150×150 µm². In some embodiments, the pixel size is less than 250×250 µm². In some embodiments, the pixel size is greater than 5×5 µm².

High-energy X-ray sensor 230 includes a high-energy X-ray scintillator 231 and a light imaging sensor 232 that is closely coupled thereto. High-energy X-ray sensor 230 further includes sensor-to-electronics interconnects 234 that connect each of a plurality pixel sensors in light imaging sensor 232 to readout electronics 250. High-energy X-ray scintillator 231 includes a scintillator material that is excited by incident X-rays and emits light that is detected by light imaging sensor 232. High-energy X-ray scintillator 231 may include a scintillator material similar to low-energy X-ray scintillator 221 or a different scintillator material.

High-energy X-ray sensor 230 is configured to convert most or all filtered X-rays 203 that are transmitted through energy-separation filter 240 to light. The light converted from transmitted X-rays 203 is measured at each of a plurality of pixel locations on light imaging sensor 232. Thus, in some embodiments, the composition and a thickness 233 of the scintillator material of the high-energy X-ray scintillator 231 is selected to maximize the conversion of incident X-rays (i.e., filtered X-rays 203) to light that is detected by the plurality of pixel sensors in light imaging sensor 232. The light detected by light imaging sensor 232 is used to generate an X-ray image based on filtered X-rays 203. It is noted that filtered X-rays 203 have a higher mean energy than the mean energy of incident X-ray 201. Consequently, the scintillator material and thickness 233 of high-energy X-ray scintillator 231 is selected to maximize the conversion of high-energy X-rays. For example, in one embodiment, high-energy X-ray scintillator 231 includes CsI as a scintillator material having a thickness 233 of between about 500 microns to about 1000 microns.

Light imaging sensor 232 can be similar in configuration to light imaging sensor 222, and includes a plurality of light sensors, such as amorphous silicon photodiodes and/or complementary CMOS-based photodiodes. Each photodiode or other light sensor (not shown) of light imaging sensor 232 is a pixel sensor that generates a signal for a different pixel of what will eventually become a digital image. For example, in one embodiment, light imaging sensor 232 includes an array of 2880×2880 pixels and has a pixel size of 150×150 microns². Alternatively, light imaging sensor 232 includes a different number of pixels than the number of pixels included in light imaging sensor 222 of low-energy X-ray sensor 220.

The incident X-rays 201 may only pass through patient 160 (shown in FIG. 1), while filtered X-rays 203 that are received by high-energy X-ray scintillator 231 have passed through patient 160, low-energy X-ray sensor 220, and energy-separation filter 240. In some embodiments, the thickness 233 of scintillator material of high-energy X-ray scintillator 231 can be similar to the thickness 223 of scintillator material of the low-energy X-ray scintillator 221. In other embodiments, the thickness 233 of scintillator material of high-energy X-ray scintillator 231 can be different from the thickness 223 of scintillator material of the low-energy X-ray scintillator 221. In some embodiments, thickness 233 of the scintillator material of high-energy X-ray scintillator 231 is thicker than thickness 223 of the scintillator material of low-energy X-ray scintillator 221. For example, in one embodiment, thickness 233 is between about 500 microns and 1000 microns, while thickness 223 is between about 100 microns and about 550 microns. In some embodiments, thickness 233 is between about two to four times as thick as thickness 223.

Readout electronics 250 includes a readout module that is communicatively coupled to low-energy X-ray sensor 220 via sensor-to-electronics interconnects 224 and to high-energy X-ray sensor 230 via sensor-to-electronics interconnects 234. Readout electronics 250 is configured as the readout circuitry for low-energy X-ray sensor 220 and high-energy X-ray sensor 230. That is, readout electronics 250 is operable to generate digital image information for a first X-ray image based on image signals from each of the plurality of pixel sensors included in low-energy X-ray sensor 220 and digital image information for a second X-ray image based on image signals from each of the plurality of pixel sensors included in high-energy X-ray sensor 230. In some embodiments, a read-out rate of readout electronics 250 is between about 7.5 frames per second to about 30 frames per second.

In some embodiments, readout electronics 250 is configured to apply a specific gain to each such image signal. For example, in some embodiments, readout electronics 250 is configured to apply a gain of up to about 30:1 to image signals associated with the pixel sensors of low-energy X-ray sensor 220 and/or high-energy X-ray sensor 230. Alternatively or additionally, in some embodiments, readout electronics 250 is configured to selectively apply a different suitable gain to low-energy X-ray sensor 220 and/or high-energy X-ray sensor 230. For example, in some embodiments, readout electronics 250 is configured to apply one of seven (or more) discrete gains to low-energy X-ray sensor 220 and high-energy X-ray sensor 230.

In some embodiments, low-energy X-ray sensor 220 generally receives a stronger X-ray signal than high-energy X-ray sensor 230, readout electronics 250 typically applies a higher gain to image signals associated with high-energy X-ray sensor 230 than to image signals associated with low-energy X-ray sensor 220.

Energy separation filter 240 is configured to optimize or otherwise improve energy separation between X-rays incident on low-energy X-ray sensor 220 (e.g., incident X-rays 201) and X-rays incident on high-energy X-ray sensor 230 (e.g., filtered X-rays 203). More specifically, energy separation filter 240 is operable to preferentially filter (i.e., absorb and/or reflect) a greater portion of incident X-rays 201 in a lower-energy region. For example, in some embodiments, energy separation filter 240 includes a plate of material that strongly absorbs X-rays, such as copper (Cu) or aluminum (Al). The thickness of such a plate depends on the particular material selected and the difference of X-ray mean energy between low energy X-rays 201 and high energy X-rays 203. For example, in some embodiments energy separation filter 240 includes a metallic plate that is between about 0.5 mm thick and about 3.0 mm thick, which depends on the density of the metal and the energy of the incident X-rays 201. Because low energy X-rays are filtered by energy separation filter 240, the mean energy of incident X-rays 201 is lower than the mean energy of transmitted X-rays 203, as illustrated in FIG. 3.

Figure 3:
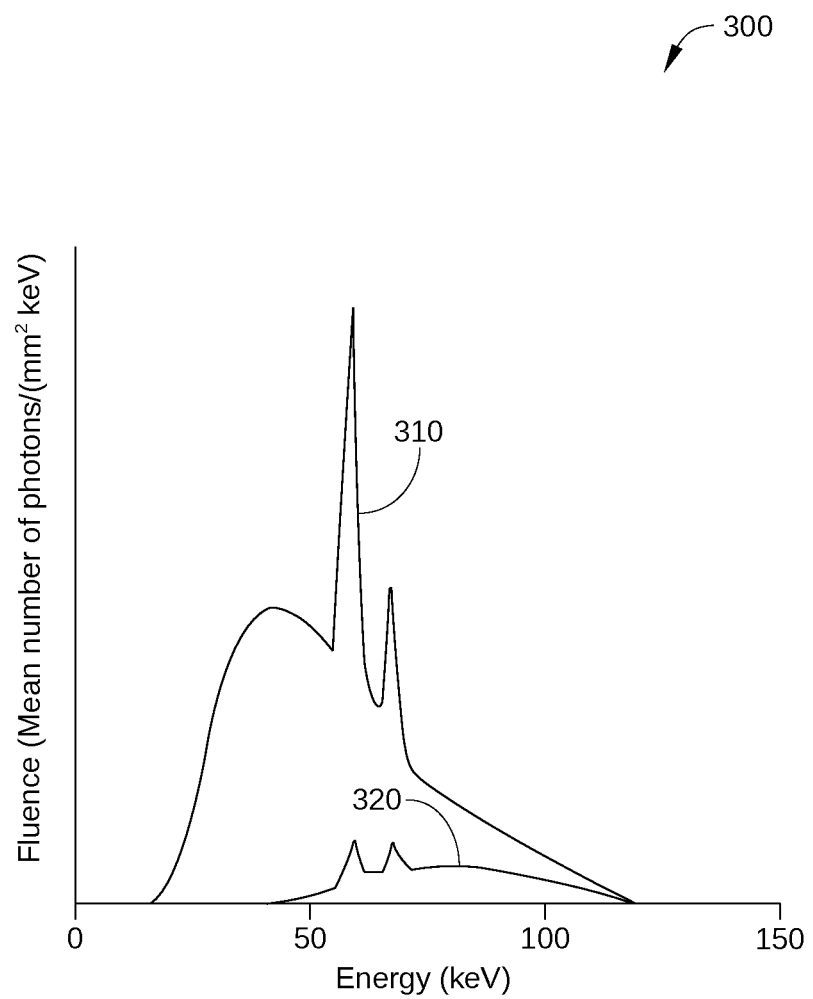
FIG. 3 is a graph comparing an energy distribution of the X-ray photons measured in incident X-rays and an energy distribution of the X-ray photons measured in transmitted X-rays, according to an embodiment of the present disclosure.

FIG. 3 is a graph 300 comparing an energy distribution 310 of the X-ray photons measured in incident X-rays 201 and an energy distribution 320 of the X-ray photons measured in transmitted X-rays 203, according to an embodiment of the present disclosure. Energy distribution 310 and energy distribution 320 each illustrate the photon fluence with respect to photon energy for a single X-ray exposure, or burst. Specifically, in the embodiment illustrated in FIG. 3, measurements associated with energy distribution 310 and energy distribution 320 are each taken in response to a single X-ray burst of imaging beam 126 (shown in FIG. 1).

For example, in one such embodiment, imaging beam 126 is generated when a peak voltage of 120 kV is applied to the X-ray tube of kV X-ray source 124.

Because transmitted X-rays 203 are attenuated relative to incident X-rays 201 by low-energy X-ray sensor 220 and energy separation 240, the total number X-rays included in transmitted X-rays 203 (represented by the area under energy distribution 320) is much smaller than the total number X-rays included in incident X-rays 201 (represented by the area under energy distribution 310). Further, for example, in one embodiment, the mean energy of incident X-rays 201 and energy distribution 310, which is approximately 60 kV, is lower than the mean energy of transmitted X-rays 203 and energy distribution 320, which is approximately 80 kV.

According to embodiments of the present disclosure, a series of soft tissue X-ray images can be generated, in which the contribution of bony structures and other high-density structures is partially or completely removed. Each of these images is generated by performing a weighted subtraction of an X-ray image generated via signals from low-energy X-ray sensor 220 from an X-ray image generated via signals from high-energy X-ray sensor 230, as illustrated in FIGS. 4A-4C.

Figure 4A:
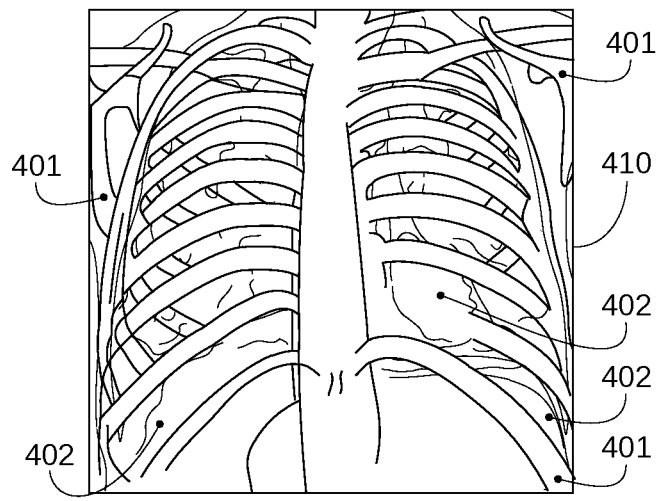
FIG. 4A schematically illustrates an X-ray image generated based on signals from low-energy X-ray sensor, according to an embodiment of the present disclosure.
Figure 4B:
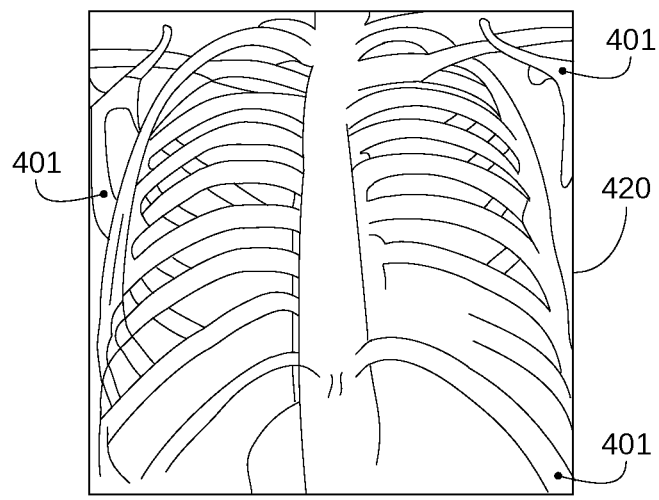
FIG. 4B schematically illustrates an X-ray image generated based on signals from high-energy X-ray sensor, according to an embodiment of the present disclosure.
Figure 4C:
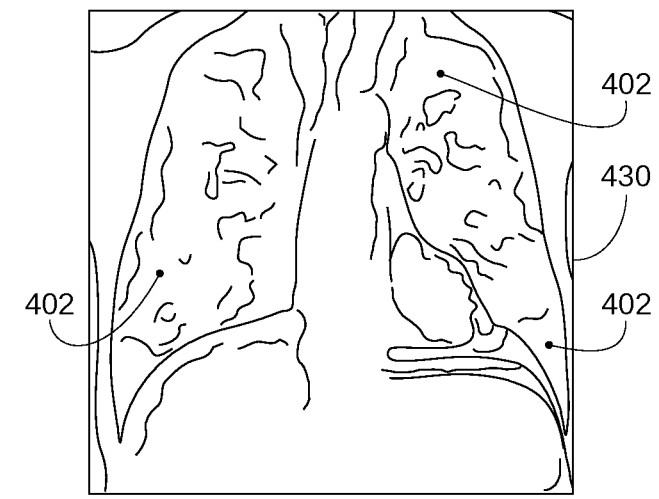
FIG. 4C schematically illustrates an X-ray image generated by performing a weighted subtraction of low-energy and high-energy X-ray images, according to an embodiment of the present disclosure.

FIG. 4A schematically illustrates an X-ray image 410 generated based on signals from low-energy X-ray sensor 220, according to one or more embodiments of the present disclosure. Thus, X-ray image 410 is generated when incident X-rays 201, which have passed through patient 160, are received by low-energy X-ray scintillator 221. As shown, bony structures 401 and soft tissue structures 402 both contribute significantly to X-ray image 410. As a result, a portion of soft tissue structures 402 are partially or completely obscured in X-ray image 410. FIG. 4B schematically illustrates an X-ray image 420 generated based on signals from high-energy X-ray sensor 230, according to one or more embodiments of the present disclosure. Thus, X-ray image 420 is generated when filtered X-rays 203, which have passed through patient 160, low-energy X-ray sensor 220, and energy-separation filter 240, are received by high-energy X-ray scintillator 231. As shown, bony structures 401 are more prominent in X-ray image 420. FIG. 4C schematically illustrates an X-ray image 430 generated by performing a weighted subtraction of X-ray image 420 from X-ray image 410, according to one or more embodiments of the present disclosure. Because the contribution of bony structures 401 have been substantially or completely removed, X-ray image 430 is essentially a soft tissue only X-ray image. As a result, in X-ray image 420, soft tissues 402 of interest, such as a tumor or other target region 162, are not obscured by bony structures 401. Consequently, X-ray image 430, when included in a series of similar X-ray images that are generated in real-time, can facilitate accurate motion detection in RT treatment.

Any technically feasible subtraction approach can be employed to remove the contribution of bony structures 401 from X-ray image 430. In some embodiments, a subtraction approach is performed on a pixel-by-pixel basis. For example, when there is a one-to-one correspondence between the pixel sensors of low-energy X-ray sensor 220 and the pixel sensors of high-energy X-ray sensor 230, a weighted subtraction is performed on digital image information for each pixel of X-ray image 401. Specifically, for each pixel in X-ray image 401, digital image information associated with a corresponding pixel from X-ray image 402 is subtracted from the pixel in X-ray image 401. In some embodiments, a logarithmic subtraction algorithm is employed. One example of a suitable logarithmic subtraction algorithm is illustrated by Expressions 1 and 2:

$$\ln(I_{soft}^{DE}) = \ln(I^H) - w_s \ln(I^L) \qquad \text{Expression 1}$$

$$\ln(I_{bone}^{DE}) = -\ln(I^H) - w_b \ln(I^L) \qquad \text{Expression 2}$$

Where $I_{soft}^{DE}$ represents a dual energy image of soft tissue, $I_{bone}^{DE}$ represents a dual energy image of hard or bony structures, $I^L$ represents a low energy X-ray image based on signals from low-energy X-ray sensor 220, $I^H$ represents a high energy X-ray image based on signals from high-energy X-ray sensor 230, $w_s$ represents a soft tissue weighting coefficient, and $w_b$ represents a hard or bony structures weighting coefficient.

In some embodiments, the soft tissue weighting factor of the above example logarithmic subtraction algorithm is determined by Expression 3:

$$w_s = \frac{\mu_{bone}^H}{\mu_{bone}^L} \qquad \text{Expression 3}$$

Where $\mu_{bone}^H$ represents an attenuation coefficient of high energy X-ray in hard or bony structures and $\mu_{bone}^L$ represents an attenuation coefficient of low energy X-ray in hard or bony structures. These attenuation coefficients can be obtained from the database created and maintained by National Institute of Standards and Technology (NIST).

In some embodiments, the bone weighting factor of the above example logarithmic subtraction algorithm is determined by Expression 4:

$$w_b = \frac{\mu_{soft}^H}{\mu_{soft}^L} \qquad \text{Expression 4}$$

Where $\mu_{soft}^H$ represents an attenuation coefficient of high energy X-ray in soft tissue and $\mu_{soft}^L$ represents an attenuation coefficient of low energy X-ray in soft tissue in a low energy X-ray image.

Ideally, each of the pixel sensors of light imaging sensor 222 is aligned with one (or more) corresponding pixel sensors of light imaging sensor 232. Because pixel size can be on the order of 0.1 mm, in practice, each pixel sensor of light imaging sensor 222 may not be perfectly aligned with the expected corresponding pixel sensor of light imaging sensor 232. As a result, in some embodiments, prior to normal operation, a vertical, a horizontal, and a rotation (angular) offset between light imaging sensor 222 and light imaging sensor 232 is measured and subsequently compensated for when a soft-tissue image similar to X-ray image 430 is generated. Thus, light imaging sensor 222 is registered in position relative to light imaging sensor 232 in a registration process. For example, in some embodiments, imaging of a phantom that includes vertical and horizontal alignment indicators, such as a cross-bar plastic phantom, is performed using light imaging sensor 222 and light imaging sensor 232 to generate two different images. The positions of the alignment indicators in each of the two images then enables the determination of the horizontal, vertical, and rotational offsets between light imaging sensor 222 and light imaging sensor 232. The determined horizontal, vertical, and rotational offsets are then stored locally in dual-layer X-ray detector 150 and subsequently used to compensate for misalignment present between light imaging sensor 222 and light imaging sensor 232. Specifically, each time a low-energy X-ray image is generated via light imaging sensor 222 similar to X-ray image 410 and a high-energy X-ray image is generated via light imaging sensor 232 similar to X-ray image 420, the horizontal, vertical, and rotational offsets are applied to X-ray image 420 (or to X-ray image 410) to correct the geometric deviation between light imaging sensor 222 and light imaging sensor 232. An example of one such method is described in U.S. patent application Ser. No. 15/823,533, entitled "Misalignment Compensation in Dual X-Ray Imager," filed Nov. 27, 2017. In addition, one such embodiment is described in FIG. 5.

Figure 5:
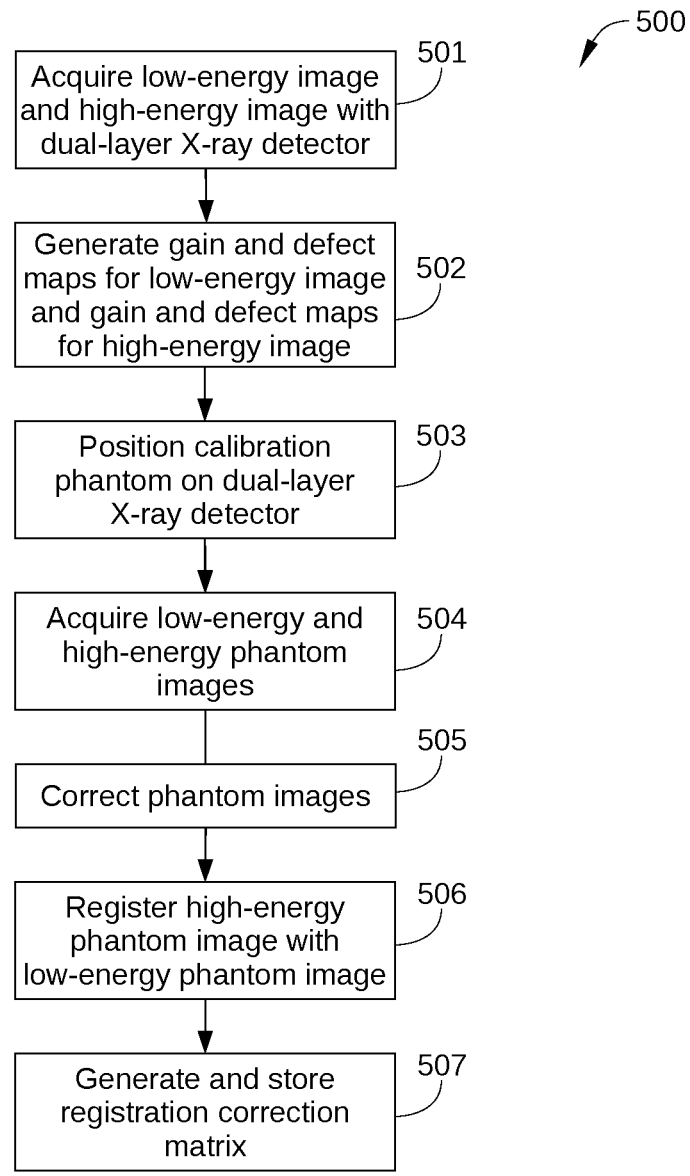
FIG. 5 sets forth a flowchart of an example method for registering a low-energy X-ray sensor and a high-energy X-ray sensor relative to each other, according to one or more embodiments of the present disclosure.

FIG. 5 sets forth a flowchart of an example method for registering low-energy X-ray sensor 220 and high-energy X-ray sensor 230 relative to each other, according to one or more embodiments of the present disclosure. The method may include one or more operations, functions, or actions as illustrated by one or more of blocks 501-507. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with clinical environment 100 and dual-layer X-ray detector 150 of FIG. 1, persons skilled in the art will understand that any suitably configured system is within the scope of the present disclosure.

A method 500 begins at step 501, a low-energy image is acquired by low-energy X-ray sensor 220 and a high-energy image is acquired by high-energy X-ray sensor 230. In step 501 the low-energy image and the high-energy image are both acquired simultaneously from the same dose of incident X-rays 201.

In step 502, a first gain map is generated for the low-energy image and a second gain map is generated for the high-energy image. In some embodiments, a first defect pixel map is also generated for the low-energy image and a second defect pixel map is generated for the high-energy image. The defect pixel maps are used to remove bad or unresponsive pixels and for generating a replacement signal for each removed pixel, for example via interpolation of signals from adjacent pixels.

In step 503, a calibration phantom is positioned on dual-layer X-ray detector 150. The calibration phantom includes a crosshair and/or other precise location indicators that are visible in images acquired by low-energy X-ray sensor 220 and high-energy X-ray sensor 230.

In step 504, a low-energy phantom image is acquired by low-energy X-ray sensor 220 and a high-energy phantom image is acquired by high-energy X-ray sensor 230. In step 504, the low-energy phantom image and the high-energy phantom image are both acquired simultaneously from the same dose of incident X-rays 201.

In step 505, the low-energy phantom image and the high-energy phantom image are each corrected. For example, offset, gain, and/or defect pixel correction (such as signal interpolation) are performed on each of the low-energy phantom image and the high-energy phantom image.

In step 506, the high-energy phantom image is registered to the low-energy phantom image. For example, in some embodiments, the location of the crosshair and/or other precise location indicators in the high-energy phantom image are compared to the crosshair and/or other precise location indicators in the low-energy phantom image. Shifts X- and Y-directions and the rotational angle between the two images are then calculated based on the comparison. Alternatively, the low-energy phantom image is registered to the high-energy phantom image.

In step 507, a registration correction matrix is generated and stored. Thus, when a low-energy image is acquired by low-energy X-ray sensor 220 and a high-energy image is acquired by high-energy X-ray sensor 230, the low-energy image and the high-energy image are each corrected by offset, gain, and defect pixel correction, then the registration correction matrix so generated can be applied to correct the geometric deviation between low-energy X-ray sensor 220 and high-energy X-ray sensor 230.

In some embodiments, method 500 is performed as part of the manufacturing process of dual-layer X-ray detector 150. In other examples, method 500 is performed periodically as part of a calibration process of the dual-layer X-ray detector 150.

Figure 6:
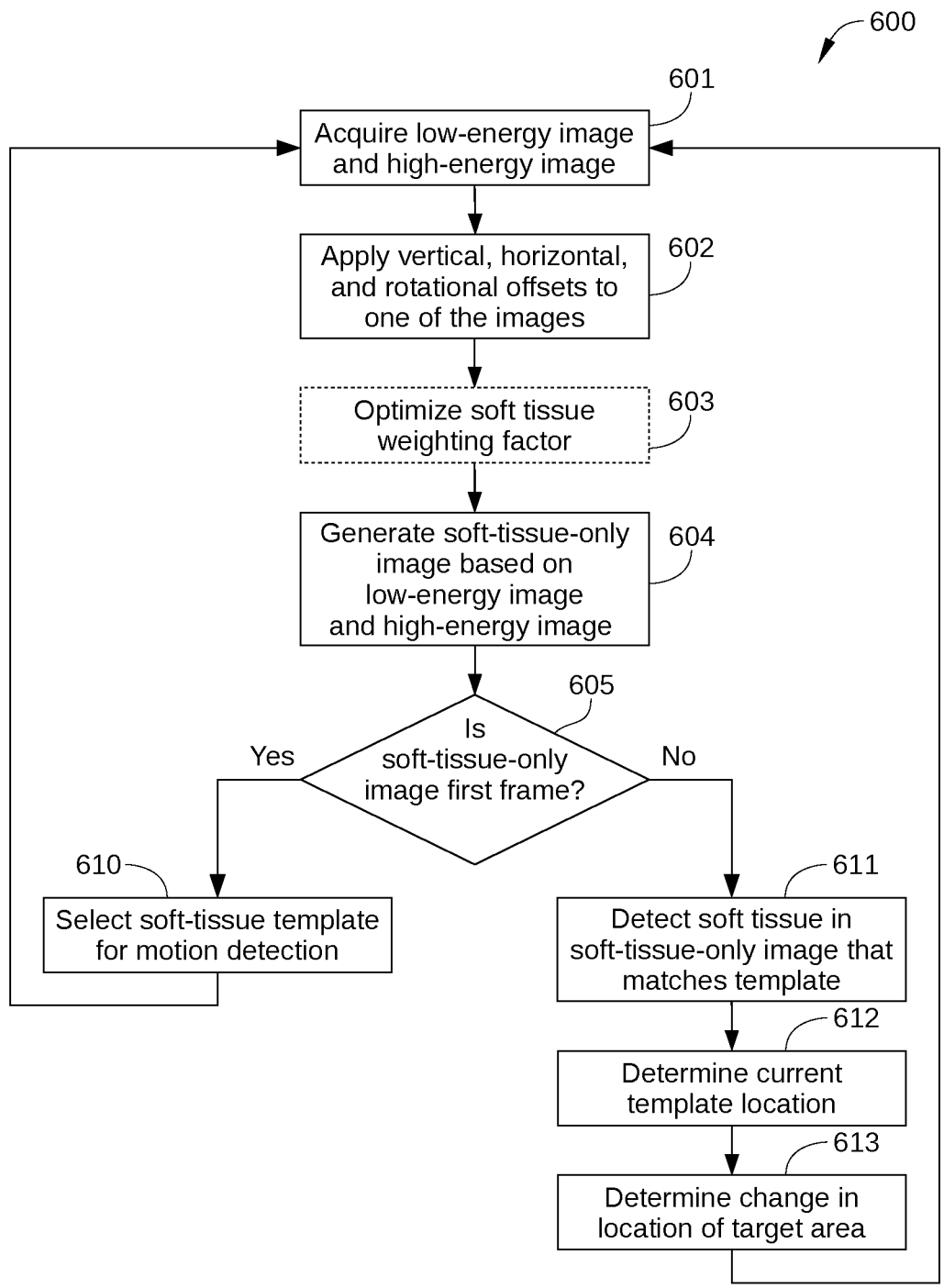
FIG. 6 sets forth a flowchart of an example method for motion tracking of a target region during RT treatment, according to one or more embodiments of the present disclosure.

FIG. 6 sets forth a flowchart of an example method for motion tracking of a target region during RT treatment, according to one or more embodiments of the present disclosure. The method may include one or more operations, functions, or actions as illustrated by one or more of blocks 601-612. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although the method is described in conjunction with clinical environment 100 and dual-layer X-ray detector 150 of FIG. 1, persons skilled in the art will understand that any suitably configured system is within the scope of the present disclosure.

In the embodiment described in conjunction with FIG. 6, the control algorithms for the method steps reside in and/or are performed by processor 280 and/or image acquisition computer 131. In other embodiments, such control algorithms may reside in and/or be performed by any other suitable control circuit or computing device.

A method 600 begins at step 601, in which a single burst of imaging beam 126 is directed toward dual-layer X-ray detector 150 for imaging target region 162 and surrounding areas during RT treatment. Thus, incident X-rays 201 are received by low-energy X-ray sensor 220 and filtered X-rays 203 are received by high-energy X-ray sensor 230. A low-energy X-ray image, similar to X-ray image 410, and a high-energy X-ray image, similar to X-ray image 420, are acquired by dual-layer X-ray detector 150. In some embodiments, as part of image acquisition, a suitable gain is applied to the signal generated by each pixel sensor of low-energy X-ray sensor 220 and high-energy X-ray sensor 230, and in some embodiments a higher gain is applied to signals associated with high-energy X-ray sensor 230 than with signals associated with low-energy X-ray sensor 220. In some embodiments, image corrections are also performed as part of image acquisition.

In step 602, dual-layer X-ray detector 150 applies suitable vertical, horizontal, rotational offsets and other geometric corrections to either the low-energy X-ray image or the high-energy X-ray image to correct the geometric deviation between light imaging sensor 222 and light imaging sensor 232.

In optional step 603, dual-layer X-ray detector 150 optimizes a soft tissue weighting factor (for use in a logarithmic subtraction algorithm). For example, in some embodiments, bone contrast is minimized or otherwise reduced.

In step 604, dual-layer X-ray detector 150 generates a soft-tissue-only X-ray image, similar to X-ray image 430, by subtracting, for each pixel of the low-energy image, a contribution value associated with the high-energy X-ray image. For example, in some embodiments, the logarithmic subtraction algorithm described above is employed in step 605.

In step 605, dual-layer X-ray detector 150 determines whether the soft-tissue-only X-ray image generated in step 604 is the first frame in a series of motion-detection images. If yes, the method proceeds to step 610; if no, the method proceeds to step 611.

In step 610, dual-layer X-ray detector 150 selects a soft tissue template for motion detection. In some embodiments, the template is selected based on automatic detection of the target area 162 for the RT treatment. In other embodiments, the template is selected based on a user input, for example via control console 132. In such embodiments, the user may trace target area 162 manually via a mouse input or touch-sensitive screen. The template is then stored in memory 290 and the method proceeds back to step 601.

In step 611, dual-layer X-ray detector 150 or image acquisition computer 131 detects target area 162 based on the stored template for the current RT treatment. Specifically, in the soft-tissue-only image generated in step 604, soft tissue that matches the stored template is detected. Any conventional image recognition algorithm or technique can be employed in step 611 to detect target area 162. Because a soft-tissue-only X-ray image similar to X-ray image 430 is employed in step 611, target area 162 is not obscured by bony structures. As a result, detection of the current location of target area 162 is more reliable and precise than in conventional approaches.

In step 612, dual-layer X-ray detector 150 or image acquisition computer 131 determines the current template location in the soft-tissue-only image.

In step 613, dual-layer X-ray detector 150 or image acquisition computer 131 determines the change in location of the template (or target area 162) in the soft-tissue-only image relative to the location of the template in an immediately preceding soft-tissue-only image of target area 162. The shift in location of the template, and therefore of target location 162, is then employed to modify the current location of MV treatment beam 122 during the RT treatment that is in progress. For example, in some embodiments, the information indicating the shift in location of the template is provided to a control system of LINAC 121 in real-time. The method then proceeds back to step 601. It is noted that an iteration of steps 601-604 and 611-613 can be performed 7.5 to 15 times per second, providing real-time feedback of changes in the location of target location 162 to LINAC 121.

Implementation of method 600 provides the advantage of more accurate visualization in image sequences of the current location of target area 162, where such image sequences may be employed for motion detection during the RT treatment. Further, such improved accuracy is not at the cost of increased imaging dose of patient 160 during RT treatment. Instead, a low-energy X-ray image and a high-energy X-ray image are generated simultaneously from a single X-ray exposure to determine the position of target area 126 at a specific time, thus the imaging dose is reduced comparing to conventional approaches.

Referring to FIGS. 1-6, some embodiments include a dual-layer X-ray detector 150 that comprises a low-energy X-ray detector 220 that includes a low-energy X-ray scintillator 221 that is operable to convert first incident X-rays 201 into a first set of light photons, a light imaging sensor 222 operable to generate a set of low energy image signals from the first set of light photons, wherein X-rays 202 are a remainder portion of first incident X-rays after the X-ray spectrum passes through low-energy X-ray scintillator (or low energy scintillator) 221 and light imaging sensor 222, energy-separation filter 240 operable to absorb or reflect at least a portion of the energy of X-rays 202 and convert the first exit X-ray spectrum into a second exit X-ray spectrum, high-energy X-ray detector 230 that includes high-energy X-ray scintillator (or high energy scintillator) 231 operable to convert X-rays 202 into a second set of light photons, light imaging sensor 232 operable to generate a set of high energy image signals from the second set of light photons; and processor 280 configured to generate a high-energy image that is based on the set of high energy image signals and a low-energy image that is based on the set of low energy image signals, and perform a comparison of the high-energy image from the low-energy image to generate a soft tissue image.

In some embodiments, a mean energy of the first incident X-rays 201 received by the low-energy X-ray detector 220 is less than a mean energy of the transmitted X-rays 202 received by the low-energy X-ray detector 220.

In some embodiments, the comparison includes a weighted subtraction.

In some embodiments, the dual-layer X-ray detector 150 further comprises a readout electronics 250 that is communicatively coupled to the low-energy X-ray detector 220 and the high-energy X-ray detector 230 and is operable to generate first digital image information based on the set of low energy image signals and second digital image information based on the set of high energy image signals.

In some embodiments, the readout electronics 250 generates the first digital image information by applying a first gain to the first set of image signals and generates the second digital image information by applying a second gain that is different from the first gain to the second set of image signals.

In some embodiments, the low-energy X-ray detector 220 and the high-energy X-ray detector 230 are operable to receive radiation simultaneously.

In some embodiments, the low-energy X-ray detector 220 and the high-energy X-ray detector 230 can acquire the images independently with separate image acquisition settings.

In some embodiments, the dual-layer X-ray detector 150 further comprises a processor 280 operable to: receive digital image information based on the first set of image signals and second digital image information based on the second set of image signals; and generate a current position of a target region 162 based on the first digital image information and the second digital image information.

In some embodiments, the processor 280 is configured to generate the current position of the target region 162 based on a difference between values included in the first digital image information and corresponding values included in the second digital image information.

In some embodiments, the processor 280 is configured to generate the current position of the target region 162 by performing a logarithmic subtraction algorithm on values included in the first digital image information and corresponding values included in the second digital image information.

In some embodiments, the processor 280 is configured to generate a soft tissue image and a bone image based on the first digital image information and the second digital image information In some embodiment, a method for motion tracking a target region 162 during a RT treatment comprises: receiving incident X-rays 201 that pass through a patient 160 that includes the target region 162; generating a first set of image signals associated with the patient 160 based on the incident X-rays 201; transmitting the X-rays 202; receiving the transmitted X-rays 202 by the energy separation filter 240; receiving the transmitted X-rays 203 by the high-energy X-ray detector 230; and generating a second set of image signals associated with the patient 160 based on the transmitted X-rays 203.

In some embodiments, the method further comprises: receiving digital image information based on the first set of image signals and second digital image information based on the second set of image signals; and generating a current position of the target region 162 based on the first digital image information and the second digital image information.

In some embodiments, generating the current position of the target region comprises generating a soft-tissue-only image of the target region based on a difference between values included in the first digital image information and corresponding values included in the second digital image information.

In some embodiments, generating the current position of the target region comprises generating a soft-tissue-only image of the target region based on a logarithmic subtraction algorithm on values included in the first digital image information and corresponding values included in the second digital image information.

In some embodiments, registering a first position of a first light imaging sensor that generates the first set of image signals relative to a second position of a second light imaging sensor that generates the second set of image signals.

In some embodiments, generating the current position of the target region further comprises applying a correction matrix to one of the first set of image signals and the second set of image signals, wherein the correction matrix is based on registering the first position of the first light imaging sensor to the second position of the second light imaging sensor.

In some embodiments, the method further comprises determining a change in location of the target region based on a current location of the soft tissue that matches the previously defined template and a previous location of the soft tissue In some embodiments, an imaging apparatus comprises: a first X-ray detecting means that is operable to: receive the incident X-rays; generate a first set of image signals based on the incident X-rays; an energy-separating means that is operable to: receive the X-rays transmitted by first X-ray detecting means; and transmit a fraction of the incident X-rays; and a second X-ray detecting means that is operable to: receive the X-rays transmitted by the energy-separating means; generate a second set of image signals based on the X-rays transmitted by the energy-separating means; and a soft tissue image generating means that is operable to generate a soft tissue image by comparing the first set of image signals to the second set of image signals In some embodiments, the imaging apparatus comprises a motion tracking means to track the motion of a target region in the soft tissue image.

Example of a first X-ray detecting means include low-energy X-ray detector 220.

Examples of a second X-ray detecting means include high-energy X-ray detector 230.

Examples of an energy-separating means include energy separation filter 240.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the claims beginning with claim [x] and ending with the claim that immediately precedes this one," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. An imaging apparatus, comprising:
   a first X-ray detector that includes:
      a low energy scintillator operable to convert an incident X-ray spectrum into a first set of light photons; and
      a first light imaging sensor operable to generate a set of low energy image signals of an imaging region that includes a target region from the first set of light photons, wherein a first exit X-ray spectrum is a remainder portion of the incident X-ray spectrum after the incident X-ray spectrum passes through the low energy scintillator and the first light imaging sensor;
   an energy-separation filter operable to absorb or reflect at least a portion of an energy of the first exit X-ray spectrum and convert the first exit X-ray spectrum into a second exit X-ray spectrum;
   a second X-ray detector that includes:
      a high energy scintillator operable to convert the second exit X-ray spectrum into a second set of light photons; and
      a second light imaging sensor operable to generate a set of high energy image signals from the second set of light photons;
   a processor configured to:
      generate a high-energy image that is based on the set of high energy image signals and a low-energy image that is based on the set of low energy, image signals; and
      perform a comparison of the high-energy image from the low-energy image to generate a soft-tissue image; and
   a readout module that is communicatively coupled to the first X-ray detector and the second X-ray detector, and is operable to generate first digital image information for generating the low-energy image that is based on the set of low energy image signals and second digital image information for generating the high-energy image based on the set of high energy image signals.

2. The imaging apparatus of claim 1, wherein the comparison includes a weighted subtraction.

3. The imaging apparatus of claim 1, wherein the energy-separation filter is configured to preferentially filter a greater portion of the first exit X-ray spectrum in a lower-energy region, so that a mean energy of the incident X-ray spectrum received by the first X-ray detector is less than a mean energy of the second exit X-ray spectrum received by the second X-ray detector.

4. The imaging apparatus of claim 1, wherein the readout module generates the first digital image information by applying a first gain to the set of low energy image signals and generates the second digital image information by applying a second gain to the set of high energy image signals, wherein the second gain is greater than or equal to the first gain.

5. The imaging apparatus of claim 1, wherein the first X-ray detector is stacked onto the second X-ray detector with the energy separation filter disposed therebetween, so that the first X-ray detector and the second X-ray detector are operable to receive at least some photons of the incident X-ray spectrum simultaneously.

6. The imaging apparatus of claim 1, further comprising a processor operable to:
receive the first digital image information and the second digital image information; and
generate a current position of a target region based on the first digital image information and the second digital image information.

7. The imaging apparatus of claim 6, wherein the processor is configured to generate the current position of the target region based on a difference between values included in the first digital image information and corresponding values included in the second digital image information.

8. The imaging apparatus of claim 6, wherein the processor is configured to generate the current position of the target region by performing a logarithmic subtraction algorithm on values included in the first digital image information and corresponding values included in the second digital image information.

9. The imaging apparatus of claim 8, wherein the processor is configured to generate a soft: tissue image and a bone image based on the first digital image information and the second digital image information.

10. The imaging apparatus of claim 1, wherein the processor is configured to track a motion of the target region using the soft tissue image by comparing the soft tissue image to a previously generated soft tissue image of the imaging region.

11. The imaging apparatus of claim 1, wherein the processor is configured to provide information indicating a shift in a location of the target region to a control system.

12. A method comprising:
receiving incident X-rays, wherein the incident X-rays pass through an imaging region that includes a target region;
generating a first set of image signals associated with the imaging region based on the incident X-rays;
transmitting first exit X-rays, wherein the first exit X-rays are a remainder portion of the incident X-rays after the incident X-rays pass through the imaging region;
converting the first exit X-rays into second exit X-rays using an energy-separation filter;
generating a second set of image signals associated with the imaging region based on the second exit X-rays; and
tracking a motion of the target region using the first set of image signals and the second set of image signals.

13. The method of claim 12, wherein tracking the motion of the target region further comprises:
receiving first digital image information based on the first set of image signals and second digital image information based on the second set of image signals; and
generating a current position of the target region based on the first digital image information and the second digital image information.

14. The method of claim 13, wherein generating the current position of the target region comprises generating a soft-tissue image of the target region based on a difference between values included in the first digital image information and corresponding values included in the second digital image information.

15. The method of claim 13, wherein generating the current position of the target region comprises generating a soft-tissue image of the target region based a logarithmic subtraction algorithm on values included in the first digital image information and corresponding values included in the second digital image information.

16. The method of claim 13, wherein generating the current position of the target region comprises registering a first position of a first light imaging sensor that generates the first set of image signals relative to a second position of a second light imaging sensor that generates the second set of image signals.

17. The method of claim 16, wherein generating the current position of the target region further comprises applying a correction matrix to one of the first set of image signals or the second set of image signals, wherein the correction matrix is based on registering the first position of the first light imaging sensor relative to the second position of the second light imaging sensor.

18. The method of claim 17, further comprising determining a change in location of the target region based on a current location of a soft tissue that matches a previously defined template and a previous location of the soft tissue.

19. An imaging apparatus, comprising:
a first X-ray detecting means that is operable to:
receive incident X-rays;
generate a first set of image signals based on the incident X-rays; and
transmit first exit X-rays;
an energy-separation means that is operable to:
receive the first exit X-rays; and
transmit second exit X-rays;
a second X-ray detecting means that is operable to:
receive the second exit X-rays transmitted by the energy-separation means; and
generate a second set of image signals based on the second exit X-rays transmitted by the energy-separation means;
a soft-tissue image generating means that is operable to generate a soft-tissue image by comparing the first set of image signals to the second set of image signals; and
a motion-tracking means that is operable to track a motion of a target region in the soft-tissue image.

* * * * *